(12) United States Patent
Richter et al.

(10) Patent No.: US 6,589,565 B1
(45) Date of Patent: Jul. 8, 2003

(54) NON-CORROSIVE STERILANT COMPOSITION

(75) Inventors: Francis L. Richter, Lino Lakes, MN (US); Duane J. Reinhardt, Maplewood, MN (US); Sally K. Swart, Inver Groves Heights, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/447,328

(22) Filed: Nov. 22, 1999

Related U.S. Application Data (60) Provisional application No. 60/109,565, filed on Nov. 23, 1998.

(51) Int. Cl.$^7$ .................. A01N 59/00; A01N 59/26; A01N 37/16; A61L 2/18
(52) U.S. Cl. .................. 424/616; 424/601; 424/606; 424/613; 424/126; 514/557; 514/558; 514/560; 514/574; 514/714; 422/28; 422/29
(58) Field of Search .................. 424/613, 616, 424/601, 606, 126; 514/557, 574, 558, 560, 714; 422/28, 29

(56) References Cited

U.S. PATENT DOCUMENTS

| | | | |
|---|---|---|---|
| 4,418,055 A | 11/1983 | Andersen et al. | 424/126 |
| 4,731,222 A | 3/1988 | Kralovic et al. | 422/37 |
| 4,892,706 A | 1/1990 | Kralovic et al. | 422/28 |
| 5,037,623 A | 8/1991 | Schneider et al. | 422/292 |
| 5,077,008 A | 12/1991 | Kralovic et al. | 422/37 |
| 5,116,575 A | 5/1992 | Badertscher et al. | 422/28 |
| 5,139,788 A * | 8/1992 | Schmidt | |
| 5,217,698 A | 6/1993 | Siegel et al. | 422/295 |
| 5,225,160 A | 7/1993 | Sanford et al. | 07/28 |
| 5,279,735 A | 1/1994 | Cosentino et al. | 210/321.69 |
| 5,350,563 A * | 9/1994 | Kralovic et al. | 422/28 |
| 5,460,962 A * | 10/1995 | Kemp | 435/238 |
| 5,508,046 A | 4/1996 | Cosentino et al. | 424/616 |
| 5,545,353 A | 8/1996 | Honda et al. | 510/176 |
| 5,552,115 A | 9/1996 | Malchesky | 422/28 |
| 5,589,507 A | 12/1996 | Hall et al. | 514/557 |
| 5,616,616 A | 4/1997 | Hall et al. | 514/557 |
| 5,634,880 A | 6/1997 | Feldman et al. | 600/132 |
| 5,635,195 A | 6/1997 | Hall et al. | 424/405 |
| 5,658,529 A | 8/1997 | Feldman et al. | 422/23 |
| 5,674,450 A | 10/1997 | Lin et al. | 422/29 |
| 5,696,686 A | 12/1997 | Sanka et al. | 364/468.17 |
| 5,716,322 A | 2/1998 | Hui et al. | 600/133 |
| 5,720,983 A | 2/1998 | Malone | 424/616 |
| 5,732,653 A | 3/1998 | Yamine | 424/613 |
| 5,733,503 A | 3/1998 | Kowatsch et al. | 422/28 |
| 5,770,739 A | 6/1998 | Lin et al. | 548/335.5 |
| 5,779,973 A | 7/1998 | Edwards et al. | 422/28 |
| 5,785,934 A | 7/1998 | Jacobs et al. | 427/29 |
| 5,788,925 A | 8/1998 | Pai et al. | 422/3 |
| 5,788,941 A | 8/1998 | Dalmasso et al. | 422/33 |
| 6,103,189 A * | 8/2000 | Kralovic | 422/28 |
| 6,468,472 B1 * | 10/2002 | Yu et al. | 422/28 |

FOREIGN PATENT DOCUMENTS

| | | |
|---|---|---|
| EP | 0 518 450 A1 | 12/1992 |
| WO | WO 95/32783 | 12/1995 |

OTHER PUBLICATIONS

Block, Seymour S. Disinfection, Sterilization, and Preservation. Lea & Febiger, Philadelphia, pp. 172–181, 1991.*
NU–CIDEX Brochure, Johnson & Johnson, pp. 1–5, 1994.*
Rutala,, W.A., et al., "Clinical Effectiveness of Low–Temperature Sterilization Technologies", Infection Control and Hospital Epidemiology, 19(10), 798–804, (Oct. 1998).

* cited by examiner

Primary Examiner—John Pak
(74) Attorney, Agent, or Firm—Merchant & Gould P.C.

(57) ABSTRACT

A non-corrosive, liquid, aqueous sterilant composition (as a concentrate or ready-to-use solution), which may be provided in two parts which are mixed prior to application, may comprise a peracid (in an equilibrium solution with an underlying carboxylic acid or mixtures of alkyl carboxylic acids and peroxide), inorganic buffering agent, and water. It has been found that the use of this simplified system, even in the absence of additional components which have been thought to be desirable for sterilants used on metal parts (e.g., copper and brass corrosion inhibitors, chelating agents, anti-corrosive agents) display excellent performance and that these additional components are not necessary, and that the presence of these additional materials at least complicates disposal of the spent solutions and could complicate compatibility of the sterilant solutions with some polymeric materials, especially where organic materials are used as the additional components, which organic materials may interact with, dissolve or solubilize in the polymeric materials.

11 Claims, 3 Drawing Sheets

NON-CORROSIVE STERILANT COMPOSITION

This application claims the benefit of U.S. Provisional application No. 60/109,565, filed Nov. 23, 1998.

NON-CORROSIVE STERILANT COMPOSITION

The present invention relates to compositions which can be used to safely and effectively disinfect surfaces and articles against microbiological forms. The compositions are easily handled, tend to be non-corrosive to the types of polymeric, elastomeric and metal surfaces found in medical instruments, are relatively shelf-stable, and may be prepared quickly and easily by simply blending component solutions.

The importance of the sterilization of medical instruments and implants has been understood for more than two centuries. The need for sterilization has become even more important recently with the appearance of strains of microbiological forms which are resistant to conventional microbiocides such as antibiotics. It has become very important to sterilize medical devices to kill or remove the more resistant strains of microbiological forms before they infect a patient. Additionally, the sterilants must be generally effective against microorganisms covering a wide range of classes and species, with U.S. Government standards requiring efficacy against both bacteria and spores.

Sterilization of medical devices has been performed for many years by immersing the medical devices in an atmosphere which is antagonistic to the survival of the microbiological forms. Among the environments which have been used to attempt to sterilize medical instruments include, but is not limited to, steam, alcohols, ethylene oxide, formaldehyde, gluteraldehyde, hydrogen peroxide, and peracids. Each of these materials has its benefits and limitations. Ethylene oxide tends to be very effective against a wide range of microorganisms, but it is highly flammable and is generally used in a gas phase which may require more stringent environmental restraints than would a liquid. Alcohols are similarly flammable and must be used in very high concentrations. Steam has a more limited utility, having to be used in a controlled and enclosed environment, requiring the use of large amounts of energy to vaporize the water, and requiring prolonged exposure periods to assure extended high temperature contact of the steam with the organisms. Hydrogen peroxide has limited applicability because it is unstable and not as strong as some other sterilants. The peracids have become more favorably looked upon, but they tend to be corrosive (being an oxidizing acid) and are not shelf stable.

U.S. Pat. No. 5,508,046 describes a stable, anticorrosive peracetic acid/peroxide sterilant comprising a concentrate including peracetic acid, acetic acid, hydrogen peroxide (in a ratio of 1:1 to 11:1 total acid/hydroxide), and 0.001 to 200 parts per million of stabilizers such as phosphonic acids and sodium pyrophosphates. The concentrates are diluted about 20 to 40 times so that the maximum concentration of stabilizer in the use solution would be about 10 parts per million. The stabilizers are described as acting as chelating agents by removing trace metals which accelerate the decomposition of the peroxides.

U.S. Pat. No. 5,616,616 describes a room temperature sterilant particularly useful with hard tap water comprising an ester of formic acid, an oxidizer (such as hydrogen peroxide or urea hydrogen peroxide), perfonuic acid and water. The use of corrosion inhibitors (such as benzotriazoles, azimidobenzene, and benzene amide) and stabilizers (unnamed) is also generally suggested.

U.S. Pat. No. 5,077,008 describes a method of removing microbial contamination and a solution for use with that method. The solution comprises a combination of five ingredients in water: 1) a strong oxidant (including, for example, organic peroxides, peracids, an chloride releasing compounds, with peracetic acid in a concentration of 0.005 to 1.0% being preferred), 2) a copper and brass corrosion inhibitor (e.g., triazoles, azoles and benzoates), 3) a buffering agent (including, for example, phosphate), 4) at least one anti-corrosive agent which inhibits corrosion in at least aluminum, carbon steel and stainless steel selected from the group consisting of chromates and dichromates, borates, phosphates, molybdates, vanadates and tungstates, and 5) a wetting agent. A sequestering agent may be used to prevent the phosphates from causing precipitation in hard water.

U.S. Pat. Nos. 4,892,706 and 4,731,22 describe automated liquid sterilization systems having a plurality of modules which store the sterilant solution and the rinse solution. U.S. Pat. No. 5.037,623 describes a sterilant concentrate injection system which is a spill resistant, vented ampule system for use with sterilization systems.

Medical devices now include many polymeric components for reasons of material costs and ease of manufacture. Many of the systems and solutions designed for the sterilization of metal medical devices are not necessarily suitable for use with polymeric components, and may cause corrosion of the polymeric materials. It is therefore necessary to formulate sterilization compositions which are compatible with both metal and polymeric components of the medical devices. It is also always desirable to provide sterilization systems with fewer components in the composition, where the sterilization solutions do not significantly sacrifice microbiocidal activity and do not corrode the materials used in medical devices.

SUMMARY OF THE INVENTION

A non-corrosive, liquid, aqueous sterilant composition (as a concentrate or ready-to-use solution), which may be provided in two parts which are mixed prior to application, may comprise a peracid (in an equilibrium solution with an underlying carboxylic acid or mixtures of alkyl carboxylic acids and peroxide), inorganic buffering agent, and water. It has been found that the use of this simplified system provides excellent sterilization ability, even in the absence of additional components which have been thought to be desirable for sterilants used on metal parts (e.g., copper and brass corrosion inhibitors, chelating agents, anti-corrosive agents) which have been found to not be necessary. The presence of these additional materials at least complicates disposal of the spent solutions and could complicate compatibility of the sterilant solutions with some polymeric materials, especially where organic materials are used as the additional components, which organic materials may interact with, dissolve or solubilize in the polymeric materials.

The concentration of the components has shown itself to be important in providing non-corrosive effects towards a wide variety of structural materials in medical devices and yet providing effective sterilization effects against spores and bacteria, including tuberculosis bacteria in an acceptable amount of time.

An aqueous sterilant use solution according to the present invention may comprise a solution having a pH of from 5.0 to 7.0 comprising from 100 to 10,000 parts per million of a peroxy acid and 30 to 5000 parts per million of buffering agent, preferably without any organic anticorrosive agents. The aqueous sterilant solution may, for example, comprise from 100 to 10,000 parts per million of a peroxy acid, 30 to 5000 parts per million of buffering agent and a catalytically effective amount of a catalyst for peroxygenation of a carboxylic acid by hydrogen peroxide.

The aqueous sterilant solution may consist essentially of a solution having a pH of from 5.0 to 7.0 comprising from 100 to 10,000 parts per million of a peroxy acid, 30 to 5000 parts per million of buffering agent and a catalytically effective amount of a catalyst for peroxygenation of a carboxylic acid by hydrogen peroxide.

The method may particularly comprise mixing a first and a second solution to form a sterilizing solution comprising a peroxy acid, said first solution comprising a carboxylic acid, hydrogen peroxide and water, and said second solution comprising a buffering agent for pH between about 5 and 7, said sterilizing solution comprising at least 100 parts per million of peroxy acid at a pH of 5 to 7, immersing said article in said sterilizing solution for at least 5 minutes to sterilize said article, said first solution and second solution being free of organic anti-corrosion agents for brass and/or copper, and said article comprising a medical article having parts made of at least two materials selected from the group consisting of metals, polymers and rubbers.

DETAILED DESCRIPTION OF THE INVENTION

The aqueous sterilant compositions of the present invention comprise a peracid, water-soluble peroxide source, and carboxylic acid in a buffered solution at pH levels between about 5.0 and 7.0. The use of an inorganic buffering agent also enables the use of slightly water-soluble, higher molecular weight carboxylic acids in the formation of peroxy acids with the peroxide source thereby reducing the amount of deposits from fatty acid residue in the solution. Phosphate buffers are effective dispersants and suspending agents for these fatty acid residues.

The peroxy acid useful in the practice of the present invention may comprise any organic peroxy acid. These acids are well known in the art to be formed from any carboxylic acid containing compound. Normally they are prepared from carboxylic acids of the formula:

$CH_3-(CH_2)n-COOH$ wherein n is 0 to 18, preferably 0 to 12 and more preferably 0 to 10, with the corresponding peroxy acid having the formula:

$CH_3-(CH_2)n-CO_3H$ wherein n is as defined above. The alkyl moiety on the acid, $CH_3-(CH_2)n-$ may be replaced with hydrogen or any, preferably low molecular weight, organic group so that the acid and the resulting peroxy acid may be represented by: $R-CO_2H$ and $R-CO_3H$, respectively. The molecular weight of R could be 1, but preferably'should be between 15 and 155.

Carboxylic acids which are generally useful in the invenetion are those which comprise percarboxylic acids. Percarboxylic acids generally have the formula $R(Co_3H_n)$, where R is an alkyl, arylaklyl, cycloalkyl, aromatic or heterocyclic group, and N is 1, 2, or 3 and named by prefixing the parent acid with peroxy.

The peracid normally exists in an equilibrium state with the original or fundamental acid and the peroxide source, usually hydrogen peroxide. Typical peracids include peracids of $C_1$ to $C_{12}$ carboxylic acids such as formic acid, acetic acid, propanoic acid, butanoic acid, pentanoic acid, hexanoic acid, heptanoic acid, octanoic acid, nonanoic acid, decanoic acid, undecanoic acid, dodecanoic acid, and the like. The term carboxylic acids as used in the practice of the present invention, unless otherwise limited, also includes mono- and di-hydroxycarboxylic acids such as glycolic acid, lactic acid and citric acid. An example of di-hydroxycarboxylic acid or di-hydroxy is tartaric acid, and also fumaric acid, which is an unsaturated di-hydroxycarboxylic acid. Diacids such as alpha-omega-dicarboxylicpropanoic acid, succinic acid, glutaric acid, adipic acid, and the like may also be used to form di-peracids. Peroxycarboxylic acids may also be present and included within the solutions of the present invention. Mixtures and combinations of the peracids may also be used in the systems of the invention, as well as other addenda as generally described herein.

The peroxide source is preferably an aqueous solution of hydrogen peroxide, but may also include such alternative peroxide sources as solutions of sodium peroxide, calcium peroxide, alkali salts of percarbonate and persulfate, and even organic peroxides such as dicumyl peroxide, dialkyl peroxides, urea peroxide, and the like, forming the basis of the solution of the hydrogen peroxide. The inorganic peroxides are preferred as the source of the solution of the hydrogen peroxide. The ratio of the peroxy acid to the hydrogen peroxide can also significantly influence the efficacy of the solutions of the invention, with higher ratios of the peroxy acid to the hydrogen peroxide preferred. For example, its is more desirable to have a ratio of at least 2:1 or 3:1 (peroxy acid to hydrogen peroxide), and more desirable to have higher ratios of at least 4:1, at least 5:1 or at least 8:1 or more (peroxy acid to hydrogen peroxide).

The buffering agent is a compound, again preferably an inorganic compound which will maintain a buffered pH level in the solution of the composition between 5.0 and 7.0. Buffering agents include, but are not limited to phosphates, borates, lactates, acetates, citrates, vanadates, tungstates, and combinations thereof, particularly alkali metal or alkaline metal salts of these agents. The use of phosphates exclusively or at least primarily (e.g., at least 50%, at least 65%, at least 75%, or at least 90 or 95% by weight of the buffering agents) is particularly useful. Trisodium phosphate has been found to be particularly desirable because of its ability to maintain the acid residues of the peroxy acids in solution where they will not form film in the solution which can be picked up by any sterilization apparatus or medical device which is being sterilized. It is interesting to note that phosphates have been generally taught to be avoided in sterilization solutions where hard water may be contacted because of the potential for calcium precipitation, yet in the present invention, the presence of phosphates reduces the formation of organic residue film on the surface of the solution. The buffering agent alone, even when a phosphate or especially when a phosphate and particularly trisodium phosphate, has been found to reduce corrosion by the solution on all surfaces. The use of phosphate(s) alone, in the absence of copper and brass corrosion inhibitors has been found to be an effective sterilant, and provide non-corrosive activity against a wide range of structural materials, including, but not limited to rubbers, plastics and metals, such as stainless steel, aluminum, polypropylene, teflon, acrylonitrile/styrene/butadiene, polyolefins, vinyl resins (e.g., polyvinyl chloride, polyvinylbutyral), silicone resins and rubbers, and polyurethanes, and provide second tier protection for brass and copper. Although the peracids work more efficiently in their microbiocidal activity at highly acidic pH levels (below 4.0), those acidic levels are much more corrosive. The use of a buffering system which maintains the pH above 5.0 and preferably between about 5.0 and 7.0 still provides a microbiocidal activity at levels which meet all international standards, using anywhere from 150 to 10,000 parts per million peracid.

The sterilant can be used as a manual system or be used in an automated system. The sterilant can be provided as a one-part or preferably two part concentrate, with the peracid in one solution and the buffer in the second solution. For example, in a two-part system, a peracid concentrate may be formed having 0.01% to 1% by weight peracid (e.g., peracetic acid), 0.003% to 1% by weight ppm hydrogen peroxide, 0.01% to 1% by weight acid (e.g., acetic acid), and the buffer solution may comprise, for example, from 0.5 to 75,000 ppm buffering agent (e.g., anhydrous trisodium phosphate) in water. Mixtures of these types of addenda, including the buffering agents and peracids, are clearly useful in the practice of the present invention. It is preferred that the concentrates have active ingredient contents at the higher levels of these ranges such as 0.1% to 15% by weight peracid, 5% to 80% by weight peroxide, 5% to 80% by weight acid and 0.1% to 15% by weight buffering agents. The diluted to use solution would preferably contain sufficient actives to provide 0.01% to 1.0% by weight peracid at a pH between about 5.0 and 7.0. The use solution need not contain any effective amount of many of the additives which prior art systems have required for non-corrosive effects (such as the organic anti-corrosive agents such as the triazines, benzotriazoles, azoles and benzoates), and yet provide a wider disclosed range of non-corrosivity against the many available surfaces of medical devices. The use solutions of the present invention may comprise a simplest solution comprising peracid (along with the acid and peroxide in equilibrium), buffering agent in an amount to provide a pH of from about 5.0 to 7.0, and water (preferably deionized water). This solution may be modified by the addition of individual agents such as chelating agents, surfactants (also referred to in the literature for sterilant compositions as wetting agents), and anti-corrosion agents. A typical concentrate solution which may be diluted to a use solution might comprise, 0.1% to 15% by weight peracid, 0.1% to 15% by weight buffering agent[, with the remainder as water and other addenda as generally described herein (e.g., from 99.6 to 78% by weight water). These and other aspects of the invention will be further described by reference to the following, non-limiting examples.

These data show that a preferred range for the concentration of peroxide in the solution (particularly as evidenced by hydrogen peroxide) less than 150 ppm, preferably less than 100 up to 80,000 ppm, still more preferably less than 100, less than 75 and less than 50 ppm. In the examples, POAA represents peroxyacetic acid, AA represents acetic acid, POOA represents peroxyoctanoic acid, and Oct. Acid represents octanoic acid. Dequest™ are commercially available materials which may be used in the solutions of the present invention. Dequest™ 2000 comprises aminotri (methylene-phosphonic acid), Dequest™ 2010 comprises 1-hydroxyethylidene-1,1-diphosphonic acid, and Dequest™ 2006 comprises aminotri(methylene-phosphonic acid) pentasodium salt. Dequest acts as a chelator for heavy metals. The data also shows that sporicidal activity of compositions with higher molecular weight peracids increase with higher proportions of the peracid as compared to the acid.

The presence of a catalyst for the formation of the peracid in the sterilization compositions of the present invention also is a novel aspect of the present invention which could act to maintain the level of peracid in the solution during use.

Corrosion Example I

Experimental

In the following comparison example, a formulation according to the present invention comprising 2.69 weight percent of a 13% solution of peracetic acid made by combining 78% glacial acetic acid, 21% hydrogen peroxide (35% by weight in water), and 1% hydroxyethylenediamine phosphonate was compared to a commercial sterilization formulation (CSF) comprising a mixture of sodium perborate and tetraacetyl ethylenediamine with a buffer to provide a use solution of pH 8, with its necessary sterilization activator. The CSF composition (referred to as Powder PAA) comprises a powder source of peracetic acid (with a solid peroxide source) without a buffering agent, and was compared to a liquid solution of peracetic acid (PAA) made according to the present invention (referred to as Liquid PAA) by admixture of acetic acid and hydrogen peroxide solution with 1% by weight of hydroxyethylenediamine phosphonate catalyst to form the solution of peracetic acid (with the equilibrium amounts of acetic acid and hydrogen peroxide) at a pH of 6.0 provided by 3.0% by weight trisodium phosphate. This commercial CSF product requires mixing of a dry powder, with a delay required for the activator TAED (tetra acetyl ethylene diamine) by reaction with sodium perborate to generate peracetic acid and microbiocidal activity in the components.

Test Parameters

The test was performed on pieces of an Olympus flexible endoscopes using a washer/disinfector to reduce manual variables. The test parameters were room temperature conditions, with the following immersion times:

| Sample | Cycles | Immersion Time |
|---|---|---|
| Liquid PAA | 1 | 10 minutes |
| Powder PAA | 1 | 15 minutes |

| Sample | Application Time |
|---|---|
| Liquid PAA | 24 hours |
| Powder PAA | 8 hours |

The test was performed by completely immersing separate test pieces S1 to S7 and W1 to W28 in each of the solutions.

Test Pieces

| Item | Parts |
|---|---|
| S1–S7 | Parts of endoscope |
| S8 and S9 | Insertion tube |
| S10 | Light guide tube |
| W1–W28 | Parats of washer/disinfector |

| Sample No. | Material (base) | Surface Control | Place of the Parts |
|---|---|---|---|
| S1 | A5056BD-H32 Resin | black painting | connector to LS |
| S2 | Polysulfone | black painting | main body |
| S3 | SUS304 Resin | El. black coating | outside (hidden) |
| S4 | Silicone Rubber | — | outside |
| S5 | Polybutadiene PB-60 | — | outside |
| S6 | Mod. PPO Polyphenyleneoxide | black painting | main body |

-continued

| Sample No. | Material (base) | Surface Control | Place of the Parts |
|---|---|---|---|
| S7 | A5056BD-H32 Resin | black alumite | eyepiece |
| S | Polyurethane | primary coat Z | insertion tube |
| S | Polyurethane | primary coat V | insertion tube |
| S | Polyurethane | | light guide cable |
| W1 | Stainless Steel | | inner pipe system |
| W2 | Stainless Steel | | inner pipe system |
| W3 | epoxy resin + coating | | heating panel |
| W4 | Polyethylene | | basin |
| W5 | Polypropylene | | basin |
| W6 | Polyacetate | | connector |
| W7 | Polysulfone | | part of top cover |
| W8 | Silicone Rubber | | sealing |
| W9 | Polyvinyl chloride | | inner pipe system |
| W10 | Polyvinyl chloride (hard) | | inner pipe system |
| W11 | Acrylic polymer | | parts in the basin |
| W12 | Ethylene/propylene | | inner pipe system |
| W13 | Ethylene/propylene rubber | | inner pipe system |
| W14 | Acrylate modified PolyVinylChloride | | top cover |
| W15 | Butyl-nitrile rubber + Phenol | | parts in the basin |
| W16 | Teflon | | name plate in basin |
| W17 | Butyl-nitrile rubber | | sealing |
| W18 | Polyurethane | | ? |
| W19 | Acrylonitrile/butadiene/styrene | | top cover |
| W20 | modified PPO | | top cover |
| W21 | Butyl rubber | | sealing |
| W22 | fluorinated rubber | | sealing |
| W23 | alumina ceramic | | parts of pump system |
| W24 | Teflon | | parts of pump system |
| W24 | Teflon rubber | | parts of pump system |

The samples were carefully inspected to evaluate the cosmetic effects (corrosion effects) on the various pieces. The first examination (Item 1) was for parts of the endoscope. The second examination (Item 2) was for the insertion tube. The third examination (Item 3) was for the light guide tube. The fourth examination (Item 4) was for the washer/disinfector. The samples performed substantially identically, with both solutions showing only a slight cosmetic change in painted black surface of the endoscope (S3 surface). No functional or cosmetic changes were noted on any other sample. The simplicity of use for the Liquid PAA system was very noteworthy, with no delay in mixing or reaction time. The solutions could be directly added into an automated system while the CSF Powder PAA system would have required premixing and activation time before it could have been used in an automatic system.

Corrosion Example II

Experimental

A corrosion study was performed to evaluate peracid containing formulas with and without buffer addition upon selected metals, plastics and rubbers.

Testing was conducted with two peracid formulation of 500 ppm (parts per million) peracetic acid (A) and 5000 ppm peracetic acid (B) concentration with buffer; and, two identical formulas (C and D respectively) with exception of no buffer addtion admixture.

Coupons were completely immersed in 200 mls of defined test solution contained in covered 8 ounce glass jars maintained at 50° C. within an environmental chamber. Solutions were changed daily. Study was conducted over a 14 day time period. For each test material, a control was also run which is a coupon of stated material placed within a covered 8 ounce glass jar having no test solution.

Coupons were pretreated before the corrosion study began, and postreated before final comparitive measurements and visual observations were performed. Metal coupons were precleaned according to ASTM Vol. 3.02, G31–72 and 3.02, G1–90 protocol and post-treated accordingly prior to final measurement. Test conditions were modified from the ASTM protocol as explained in above paragraph. Plastic and rubber coupons were only rinsed with deionized water and air dried prior to corrosion study; and, similarly treated prior to final measurement and visual observation.

Conclusion

Addition of buffer admixture to peracetic acid composition test solutions significantly improves metals protection. The effect is less noticeable on test plastics; but, protection is provided selected test rubbers.

PART IA: FORMULA—PERACID COMPONENT

HIGH POAA—LOW H202 PEPACID FORMULA KX-6091

| ITEM | RAW MATERIAL | WT % | GM/ 10000 |
|---|---|---|---|
| 10 | Acetic Acid | 78.00 | 7800.00 |
| 20 | Hydrogen Peroxide 35% | 21.00 | 2100.00 |
| 30 | Dequest ™ 2010 (60%) | 1.00 | 100.00 |
| | Total | 100.00 | 10000.00 |

Mixing Instructions:

Batch was prepared by direct weighing on Mettler PM 16 Top Loading Balance into a 5 gal HMW/HDPE (high molecular weight/high density polypropylene) pail. The batch was mixed for 65 minutes using a lab mixer equipped with a plastic coated stir rod and blade.

PART IB: FORMULA - ADMIXTURE OF IA AND BUFFER COMPONENT FORMULAS A, B, C, D CORROSION STUDY USE DILUTIONS

| | | (A) | | (B) | | (C) | | (D) | |
|---|---|---|---|---|---|---|---|---|---|
| ITEM | Material | WT % | GM/ 4500 | WT % | GM/ 4500 | WT % | GM/ 4500 | WT % | GM/ 4500 |
| 10 | Deionized Water | 99.10556 | 4459.75 | 90.66311 | 4079.84 | 99.55756 | 4480.09 | 95.57511 | 4300.88 |

-continued

PART IB: FORMULA - ADMIXTURE OF IA
AND BUFFER COMPONENT
FORMULAS A, B, C, D
CORROSION STUDY USE DILUTIONS

| | | | | | | | | | |
|---|---|---|---|---|---|---|---|---|---|
| 20 | Trisodium Phosphate Anhyd. Gran. | 0.45200 | 20.41 | 4.91200 | 221.04 | | | | |
| 30 | KX-6091 (11.3% POAA) | 0.44244 | 19.91 | 4.42489 | 199.12 | 0.44244 | 19.91 | 4.42489 | 199.12 |
| | Total | 100.00000 | 4500.07 | 100.00000 | 4500.00 | 100.00000 | 4500.00 | 100.00000 | 4500.00 |

| THEORETICAL VALUES | ppm | pH | ppm | pH | ppm | pH | ppm | pH |
|---|---|---|---|---|---|---|---|---|
| POAA | 500 | 6.00 | 5000 | 6.00 | 500 | 3.00 | 5000 | 2.50 |

INSTRUCTIONS
Add Trisodium Phosphate Anhydrous Granules (item 20) by wt. to weighed amount of DI water and stir with Lab mixer until dissolved. Add (item 30) by wt. to buffered water and final mix 2 min.
RESULTS:
(A) - pH = 6.02
(B) - pH = 5.99
(C) - pH = 2.96
(D) - pH = 2.35

PART II: CORROSION - METALS
14 day Compatibility Test of 15 different materials tested against four different Test Solutions at 50° C. with the test solutions are changed daily.

| Test item | Test Solution | Material METALS | Initial Wt. (gms) | Final Wt. (gms) | TWL | CWL | AWL | mpy |
|---|---|---|---|---|---|---|---|---|
| 1 | (A) 500 ppm POAA/Buffered | 316 SS | 23.5792 | 23.5791 | 0.0001 | 0.0001 | 0.0000 | 0.0000 |
| 5 | (B) 5000 ppm POAA/Buffered | 316 SS | 23.5194 | 23.5193 | 0.0001 | 0.0001 | 0.0000 | 0.0000 |
| 9 | (C) 500 ppm POAA only | 316 SS | 23.5764 | 23.5762 | 0.0002 | 0.0001 | 0.0000 | 0.0031 |
| 13 | (D) 5000 ppm POAA only | 316 SS | 23.5690 | 23.5689 | 0.0001 | 0.0001 | 0.0000 | 0.0000 |
| 17 | CONTROL | 316 SS | 23.5846 | 23.5845 | 0.0001 | 0.0001 | | |
| 2 | (A) 500 ppm POAA/Buffered | 304 SS | 17.9651 | 17.9650 | 0.0001 | 0.0000 | 0.0001 | 0.0031 |
| 6 | (B) 5000 ppm POAA/Buffered | 304 SS | 17.9326 | 17.9323 | 0.0003 | 0.0000 | 0.0030 | 0.0938 |
| 10 | (C) 500 ppm POAA only | 304 SS | 17.9795 | 17.9793 | 0.0002 | 0.0000 | 0.0002 | 0.0063 |
| 14 | (D) 5000 ppm POAA only | 304 SS | 17.9993 | 17.9992 | 0.0001 | 0.0000 | 0.0001 | 0.0031 |
| 18 | CONTROL | 304 SS | 18.1102 | 18.1102 | 0.0000 | 0.0000 | | |
| 3 | (A) 500 ppm POAA/Buffered | 7075 Aluminum | 12.8716 | 12.8685 | 0.0031 | 0.0002 | 0.0029 | 0.2412 |
| 7 | (B) 5000 ppm POAA/Buffered | 7075 Aluminum | 12.7575 | 12.7336 | 0.0239 | 0.0002 | 0.0237 | 1.9712 |
| 11 | (C) 500 ppm POAA only | 7075 Aluminum | 12.8651 | 12.8392 | 0.0259 | 0.0002 | 0.0257 | 2.1376 |
| 15 | (D) 5000 ppm POAA only | 7075 Aluminum | 12.8718 | 12.7439 | 0.1279 | 0.0002 | 0.1277 | 10.6213 |
| 19 | CONTROL | 7075 Aluminum | 12.4899 | 12.4897 | 0.0002 | 0.0002 | | |
| 4 | (A) 500 ppm POAA/Buffered | 260 Brass | 26.4108 | 26.3763 | 0.0345 | 0.0004 | 0.0341 | 0.9779 |
| 8 | (B) 5000 ppm POAA/Buffered | 260 Brass | 26.4211 | 26.3307 | 0.0904 | 0.0004 | 0.0900 | 2.5809 |
| 12 | (C) 500 ppm POAA only | 260 Brass | 26.6471 | 25.6695 | 0.9776 | 0.0004 | 0.9772 | 28.0233 |
| 16 | (D) 5000 ppm POAA only | 260 Brass | 26.4949 | 18.9759 | 7.5190 | 0.0004 | 7.5186 | 215.6118 |
| 20 | CONTROL | 260 Brass | 26.4352 | 26.4348 | 0.0004 | 0.0004 | | |

| Test item | Test Solution | Material METALS | Visual Observations |
|---|---|---|---|
| 1 | (A) 500 ppm POAA/Buffered | 316 SS | Smooth, shiny silver colored material like control |
| 5 | (B) 5000 ppm POAA/Buffered | 316 SS | Smooth, shiny silver colored material like control |
| 9 | (C) 500 ppm POAA only | 31 6 SS | Smooth, shiny silver colored material like control |
| 13 | (D) 5000 ppm POAA only | 316 SS | Smooth, shiny silver colored material like control |
| 17 | CONTROL | 316 SS | Smooth, shiny silver colored material |
| 2 | (A) 500 ppm POAA/Buffered | 304 SS | Smooth, shiny silver colored material like control |
| 6 | (B) 5000 ppm POAA/Buffered | 304 SS | Smooth, shiny silver colored material like control |
| 10 | (C) 500 ppm POAA only | 304 SS | Smooth, shiny silver colored material like control |
| 14 | (D)5000 ppm POAA only | 304 SS | Smooth, shiny silver colored material like control |
| 18 | CONTROL | 304 SS | Smooth, shiny silver colored material |

PART II: CORROSION - METALS
14 day Compatibility Test of 15 different materials tested against four different Test Solutions at 50° C. with the test solutions are changed daily.

| | | | |
|---|---|---|---|
| 3 | (A) 500 ppm POAA/Buffered | 7075 Aluminum | A slt. duller, slt. whiter than control, silver material |
| 7 | (B) 5000 ppm POAA/Buffered | 7075 Aluminum | A very dull, smokey brown colored material |
| 11 | (C) 500 ppm POAA only | 7075 Aluminum | A dull, whitish gray colored material |
| 15 | (D) 5000 ppm POAA only | 7075 Aluminum | A very dull, very whitish gray colored material |
| 19 | CONTROL | 7075 Aluminum | A slt. dull, silver colored material |
| 4 | (A) 500 ppm POAA/Buffered | 260 Brass | A mixture of dull gold & pink area colored material |
| 8 | (B) 5000 ppm POAA/Buffered | 260 Brass | A dull, gold colored material with patches of pink |
| 12 | (C) 500 ppm POAA only | 260 Brass | A darker dull gold colored material with pink areas |
| 16 | (D) 5000 ppm POAA only | 260 Brass | A sparkling grainy gold colored material |
| 20 | CONTROL | 260 Brass | A smooth, shiny, gold colored material |

KX-6091 CORROSION STUDY CALCULATION DATA

| | DENSITY | AREA in inches squared |
|---|---|---|
| 4 Metals | | |
| 316 Stainless Steel | 7.98 | 6.5 |
| 304 Stainless Steel; | 7.94 | 6.4 |
| 7075 Aluminum | 2.81 | 6.8 |
| 260 Brass | 8.5 | 6.52 |
| Time & Temp Tested | | |
| 14 days at 50° C. | | | mpy = (534,000 * AWL)/(A * T * D)
(A) = Area (see above)
(T) = Time (336 hrs)
(D) = Density (see above)
AWL = TWL − CWL
TWL = Pre-testing weight − Post-testing weight
CWL = Pre-testing weight of control − Post-testing weight of control
mpy = mils per year

PART III: CORROSION - PLASTICS
Analytical - Observations
KX-6091 CORROSION STUDY
14 day Compatibility Test of 15 different materials tested against four different Test Solutions at 50° C. with the test solutions are changed daily.

| Test item | Test Solution | Material PLASTICS | Initial Wt. (gms) | Initial Ht. (inches) | Initial Width (Inches) | Initial Thick (inches) | Final Wt. (gms) | % Weight Change |
|---|---|---|---|---|---|---|---|---|
| 21 | (A) 500 ppm POAA/Buffered | Polyurethane | 3.8348 | 2.996 | 0.506 | 0.128 | 3.8360 | 0.0313 |
| 27 | (B) 5000 ppm POAA/Buffered | Polyurethane | 3.8379 | 2.996 | 0.502 | 0.129 | 3.8385 | 0.0156 |
| 33 | (C) 5000 ppm POAA only | Polyurethane | 3.8385 | 2.999 | 0.505 | 0.128 | 3.8418 | 0.0860 |
| 39 | (D) 5000 ppm POAA only | Polyurethane | 3.8151 | 2.995 | 0.504 | 0.127 | 3.7411 | −1.9397 |
| 45 | CONTROL | Polyurethane | 3.8286 | 2.996 | 0.505 | 0.128 | 3.8200 | −0.2248 |
| 22 | (A) 500 ppm POAA/Buffered | Polyethylene | 1.3741 | 2.991 | 0.505 | 0.066 | 1.3736 | −0.0364 |
| 28 | (B) 5000 ppm POAA/Buffered | Polyethylene | 1.3676 | 2.991 | 0.505 | 0.064 | 1.3675 | −0.0073 |
| 34 | (C) 500 ppm POAA only | Polyethylene | 1.3541 | 2.992 | 0.504 | 0.065 | 1.3541 | 0.0000 |
| 40 | (D) 5000 ppm POAA only | Polyethylene | 1.3586 | 2.995 | 0.504 | 0.066 | 1.3593 | 0.0515 |
| 46 | CONTROL | Polyethylene | 1.3668 | 2.991 | 0.504 | 0.068 | 1.3667 | −0.0073 |
| 23 | (A) 500 ppm POAA/Buffered | Polypropylene | 1.3792 | 3.002 | 0.504 | 0.066 | 1.3792 | 0.0000 |

-continued

PART III: CORROSION - PLASTICS
Analytical - Observations
KX-6091 CORROSION STUDY
14 day Compatibility Test of 15 different materials tested against four different Test
Solutions at 50° C. with the test solutions are changed daily.

| | | | | | | | | |
|---|---|---|---|---|---|---|---|---|
| 29 | (B) 5000 ppm POAA/Buffered | Polypropylene | 1.3774 | 2.998 | 0.503 | 0.065 | 1.3775 | 0.0073 |
| 35 | (C) 500 ppm POAA only | Polypropylene | 1.3793 | 2.998 | 0.504 | 0.065 | 1.3796 | 0.0218 |
| 47 | CONTROL | Polypropylene | 1.3812 | 2.997 | 0.503 | 0.065 | 1.3811 | −0.0072 |
| 24 | (A) 500 ppm POAA/Buffered | Polyvinyl Chloride | 2.1801 | 3.002 | 0.505 | 0.066 | 2.1843 | 0.1927 |
| 30 | (B) 5000 ppm POAA/Buffered | Polyvinyl Chloride | 2.2005 | 2.997 | 0.505 | 0.066 | 2.2041 | 0.1636 |
| 36 | (C) 500 ppm POAA only | Polyvinyl Chloride | 2.1734 | 2.998 | 0.505 | 0.065 | 2.1777 | 0.1978 |
| 42 | (D) 5000 ppm POAA only | Polyvinyl Chloride | 2.1590 | 2.998 | 0.505 | 0.065 | 2.1625 | 0.1621 |
| 48 | CONTROL | Polyvinyl Chloride | 2.2048 | 2.999 | 0.505 | 0.056 | 2.2037 | −0.0499 |
| 25 | (A) 500 ppm POAA/Buffered | ABS | 1.4724 | 2.995 | 0.507 | 0.061 | 1.4762 | 0.2581 |
| 31 | (B) 5000 ppm POAA/Buffered | ABS | 1.5167 | 3.003 | 0.507 | 0.063 | 1.5201 | 0.2242 |
| 37 | (C) 500 ppm POAA only | ABS | 1.5082 | 3.000 | 0.507 | 0.062 | 1.5132 | 0.3315 |
| 43 | (D) 5000 ppm POAA only | ABS | 1.4971 | 2.995 | 0.505 | 0.062 | 1.5047 | 0.5076 |
| 49 | CONTROL | ABS | 1.4822 | 2.995 | 0.507 | 0.062 | 1.4813 | −0.0607 |
| 26 | (A) 500 ppm POAA/Buffered | Polyacetal | 4.4596 | 3.003 | 0.507 | 0.133 | 4.5033 | 0.9799 |
| 32 | (B) 5000 ppm POAA/Buffered | Polyacetal | 4.3970 | 3.003 | 0.507 | 0.131 | 4.4302 | 0.7551 |
| 38 | (C) 500 ppm POAA only | Polyacetal | 4.4967 | 3.004 | 0.506 | 0.134 | 4.5441 | 1.0092 |
| 44 | (D) 5000 ppm POAA only | Polyacetal | 4.3832 | 3.003 | 0.507 | 0.131 | 4.4264 | 0.9856 |
| 50 | CONTROL | Polyacetal | 4.4498 | 3.002 | 0.506 | 0.133 | 4.4454 | −0.0989 |

| Test item | Final Ht. (inches) | % Height Change | Final Width (inches) | % Width Change | Final Thick (inches) | % Thick Changes |
|---|---|---|---|---|---|---|
| 21 | 2.996 | 0.0000 | 0.507 | 0.1976 | 0.128 | 0.0000 |
| 27 | 2.998 | 0.0668 | 0.502 | 0.0000 | 0.128 | −0.7752 |
| 33 | 3.004 | 0.1567 | 0.505 | −0.1976 | 0.127 | −0.7813 |
| 39 | 3.061 | 2.2037 | 0.509 | 0.9921 | 0.125 | −1.5748 |
| 45 | 2.993 | −0.1001 | 0.504 | −0.1980 | 0.128 | 0.0000 |
| 22 | 2.991 | 0.0000 | 0.504 | −0.1980 | 0.066 | 0.0000 |
| 28 | 2.991 | 0.0000 | 0.505 | 0.0000 | 0.065 | 1.5625 |
| 34 | 2.991 | −0.0334 | 0.502 | −0.3968 | 0.065 | 0.0000 |
| 40 | 2.994 | −0.0334 | 0.502 | −0.3968 | 0.066 | 0.0000 |
| 46 | 2.989 | −0.0669 | 0.504 | 0.0000 | 0.068 | 0.0000 |
| 23 | 3.001 | −0.0333 | 0.503 | −0.1984 | 0.067 | 1.5152 |
| 29 | 2.999 | 0.0334 | 0.503 | 0.0000 | 0.066 | 1.5385 |
| 35 | 2.998 | 0.0000 | 0.503 | −0.1984 | 0.065 | 0.0000 |
| 47 | 2.997 | 0.0000 | 0.503 | 0.0000 | 0.065 | 0.0000 |
| 24 | 3.002 | 0.0000 | 0.506 | 0.1980 | 0.065 | −1.5152 |
| 30 | 2.997 | 0.0000 | 0.506 | 0.1980 | 0.066 | 0.0000 |
| 36 | 2.998 | 0.0000 | 0.505 | 0.0000 | 0.065 | 0.0000 |
| 42 | 2.997 | −0.0334 | 0.505 | 0.0000 | 0.065 | 0.0000 |
| 48 | 2.998 | −0.0333 | 0.505 | 0.0000 | 0.056 | 0.0000 |
| 25 | 2.999 | 0.1336 | 0.508 | 0.1972 | 0.061 | 0.0000 |
| 31 | 3.006 | 0.0999 | 0.506 | −0.1972 | 0.063 | 0.0000 |
| 37 | 3.004 | 0.1333 | 0.508 | 0.1972 | 0.062 | 0.0000 |
| 43 | 3.000 | 0.1669 | 0.510 | 0.9901 | 0.062 | 0.0000 |
| 49 | 2.995 | 0.0000 | 0.508 | 0.1972 | 0.062 | 0.0000 |
| 26 | 3.010 | 0.2331 | 0.508 | 0.1972 | 0.134 | 0.7519 |
| 32 | 3.009 | 0.1998 | 0.507 | 0.0000 | 0.132 | 0.7634 |
| 38 | 3.014 | 0.3329 | 0.508 | 0.3953 | 0.135 | 0.7463 |
| 44 | 3.012 | 0.2997 | 0.508 | 0.1972 | 0.132 | 0.7634 |
| 50 | 3.000 | −0.0666 | 0.506 | 0.0000 | 0.133 | 0.0000 |

| Test item | Test Solution | Material PLASTICS | Visual Observations |
|---|---|---|---|
| 21 | (A) 500 ppm POAA/Buffered | Polyurethane | Dull opaque orange material with semi-transparent boarder |
| 27 | (B) 5000 ppm POAA/Buffered | Polyurethane | Dull opaque orange material with semi-transparent boarder |

PART III: CORROSION - PLASTICS
Analytical - Observations
KX-6091 CORROSION STUDY
14 day Compatibility Test of 15 different materials tested against four different Test Solutions at 50° C. with the test solutions are changed daily.

|    |                          |                     |                                                                                                |
|----|--------------------------|---------------------|------------------------------------------------------------------------------------------------|
|    |                          |                     | and slt. tacky                                                                                 |
| 33 | (C) 500 ppm POAA only    | Polyurethane        | Dull darker opaque orange material with semi-transparent boarder and slt. tacky                |
| 39 | (D) 5000 ppm POAA only   | Polyurethane        | Very dark orange, very tacky, completely opaque material that stuck to drying surface resulting in loss of material |
| 45 | CONTROL                  | Polyurethane        | A dull, dirty, slt. yellow tinted, semi-transparent material                                   |
| 22 | (A) 500 ppm POAA/Buffered| Polyethylene        | Slt. whiter material than control                                                              |
| 28 | (B) 5000 ppm POAA/Buffered| Polyethylene       | Slt. whiter material than control                                                              |
| 34 | (C) 500 ppm POAA only    | Polyethylene        | Slt. whiter material than control                                                              |
| 40 | (D) 5000 ppm POAA only   | Polyethylene        | Slt. whiter material than control                                                              |
| 46 | CONTROL                  | Polyethylene        | A dull, grayish white material                                                                 |
| 23 | (A) 500 ppm POAA/Buffered| Polypropylene       | A white filmy, faintly transparent, more cloudy material than control                          |
| 29 | (B) 5000 ppm POAA/Buffered| Polypropylene      | A white filmy, faintly transparent, more cloudy material than control                          |
| 35 | (C) 500 ppm POAA only    | Polypropylene       | A white heavy filmed, faintly transparent, more cloudy material than control                   |
| 41 | (D) 5000 ppm POAA only   | Polypropylene       | A white filmy, faintly transparent, more cloudy material than control                          |
| 47 | CONTROL                  | Polypropylene       | A dull gray, semi-transparent material                                                         |
| 24 | (A) 500 ppm POAA/Buffered| Polyvinyl Chloride  | Slt. less shiny and slt. less dark gray material than control                                  |
| 36 | (C) 500 ppm POAA only    | Polyvinyl Chloride  | A dull med. gray material                                                                      |
| 42 | (D) 5000 ppm POAA only   | Polyvinyl Chloride  | A dull light to medium gray material                                                           |
| 48 | CONTROL                  | Polyvinyl Chloride  | A dark, shiny gray material                                                                    |
| 25 | (A) 500 ppm POAA/Buffered| ABS                 | A slt. dull, whiter material than control                                                      |
| 31 | (B) 5000 ppm POAA/Buffered| ABS                | A slt. dull, whiter material than control                                                      |
| 37 | (C) 500 ppm POAA only    | ABS                 | A slt. dull, much whiter white material than control                                           |
| 43 | (D) 5000 ppm POAA only   | ABS                 | A slt. dull bright white material                                                              |
| 49 | CONTROL                  | ABS                 | A slt. dull, vanilla white material                                                            |
| 26 | (A) 500 ppm POAA/Buffered| Polyacetal          | A dull, cleaner white appearance than control                                                  |
| 32 | (B) 5000 ppm POAA/Buffered| Polyacetal         | A dull, cleaner white appearance than control                                                  |
| 38 | (C) 500 ppm POAA only    | Polyacetal          | A dull, cleaner white appearance than control                                                  |
| 44 | (D) 5000 ppm POAA only   | Polyacetal          | A dull, cleaner white appearance than control                                                  |
| 50 | CONTROL                  | Polyacetal          | A dull, dirty white material                                                                   |

PART IV: CORROSION - RUBBERS
Analytical - Observations
KX-6091 CORROSION STUDY
14 day Compatibility Test of 15 different materials tested against four different Test Solutions at 50° C. with the test solutions are changed daily.

| Test item | Test Solution | Material RUBBERS | Initial Wt. (gms) | Initial Ht. (inches) | Initial Width (inches) | Initial thick (inches) | Final Wt. (gms) | % Weight Change |
|---|---|---|---|---|---|---|---|---|
| 51 | (A) 500 ppm POAA/Buffered | Silicone | 14.2724 | 2.930 | 0.928 | 0.254 | 14.2553 | −0.1198 |
| 56 | (B) 5000 ppm POAA/Buffered | Silicone | 15.5707 | 2.999 | 1.007 | 0.249 | 15.5665 | −0.0270 |
| 61 | (C) 500 ppm POAA only | Silicone | 15.6958 | 3.013 | 0.995 | 0.252 | 15.7755 | 0.5078 |
| 66 | (D) 5000 ppm POAA only | Silicone | 15.1443 | 2.977 | 0.994 | 0.246 | 15.3760 | 1.5299 |
| 71 | CONTROL | Silicone | 15.6702 | 2.970 | 1.001 | 0.253 | 15.6417 | −0.1819 |
| 52 | (A) 500 ppm POAA/Buffered | Butyl | 1.9074 | 2.999 | 0.507 | 0.069 | 1.9852 | 4.0789 |
| 57 | (B) 5000 ppm POAA/Buffered | Butyl | 1.9082 | 2.999 | 0.505 | 0.069 | 1.9263 | 0.9485 |
| 62 | (C) 500 ppm POAA only | Butyl | 1.9026 | 2.996 | 0.505 | 0.068 | 2.0729 | 8.9509 |
| 67 | (D) 5000 ppm POAA only | Butyl | 1.9097 | 2.998 | 0.507 | 0.069 | 2.2216 | 16.3324 |
| 72 | CONTROL | Butyl | 1.9001 | 2.998 | 0.507 | 0.069 | 1.8939 | −0.3263 |
| 53 | (A) 500 ppm POAA/Buffered | Vison | 23.3725 | 3.057 | 1.031 | 0.248 | 23.4407 | 0.2918 |

-continued

PART IV: CORROSION - RUBBERS
Analytical - Observations
KX-6091 CORROSION STUDY
14 day Compatibility Test of 15 different materials tested against four different Test
Solutions at 50° C. with the test solutions are changed daily.

| | | | | | | | | |
|---|---|---|---|---|---|---|---|---|
| 58 | (B) 5000 ppm POAA/Buffered | Vison | 21.3847 | 2.984 | 1.014 | 0.237 | 21.4843 | 0.5598 |
| 68 | (D) 5000 ppm POAA only | Vison | 22.4157 | 2.964 | 1.012 | 0.251 | 23.7728 | 6.0542 |
| 73 | CONTROL | Vison | 22.0694 | 2.988 | 1.012 | 0.244 | 22.0584 | −0.0498 |
| 54 | (A) 500 ppm POAA/Buffered | EPDM | 17.0399 | 3.042 | 1.005 | 0.277 | 17.1763 | 0.8005 |
| 59 | (B) 5000 ppm POAA/Buffered | EPDM | 16.9577 | 3.033 | 1.006 | 0.278 | 17.2265 | 1.5851 |
| 64 | (C) 500 ppm POAA only | EPDM | 16.9824 | 3.059 | 1.015 | 0.275 | 16.9653 | −0.1007 |
| 69 | (D) 5000 ppm POAA only | EPDM | 17.4875 | 2.985 | 1.072 | 0.274 | 17.9757 | 2.7917 |
| 74 | CONTROL | EPDM | 16.7254 | 2.964 | 1.016 | 0.278 | 16.6918 | −0.2009 |
| 55 | (A) 500 ppm POAA/Buffered | BUNA N | 15.8678 | 2.960 | 1.006 | 0.242 | 16.3169 | 2.8303 |
| 80 | (B) 5000 ppm POAA/Buffered | BUNA N | 15.9576 | 2.980 | 1.020 | 0.240 | 16.4275 | 2.9447 |
| 85 | (C) 500 ppm POAA only | BUNA N | 16.2737 | 2.977 | 1.016 | 0.246 | 18.9478 | 4.1423 |
| 70 | (D) 5000 ppm POAA only | BUNA N | 15.8516 | 2.956 | 1.014 | 0.242 | 16.5043 | 4.1176 |
| 75 | CONTROL | BUNA N | 16.0735 | 2.936 | 1.107 | 0.247 | 16.0328 | −0.2532 |

| Test item | Final Ht. (inches) | % Height Change | Final Width (inches) | % Width Change | Final Thick (inches) | % Thick Change |
|---|---|---|---|---|---|---|
| 51 | 2.930 | 0.0000 | 0.933 | 0.5388 | 0.254 | 0.0000 |
| 56 | 2.995 | −0.1334 | 1.008 | 0.0993 | 0.249 | 0.0000 |
| 61 | 3.019 | 0.1991 | 1.004 | 0.9045 | 0.252 | 0.0000 |
| 66 | 3.003 | 0.6734 | 1.005 | 1.1066 | 0.249 | 1.2195 |
| 71 | 2.970 | 0.0000 | 1.013 | 1.1988 | 0.254 | 0.3953 |
| 52 | 3.008 | 0.3001 | 0.507 | 0.0000 | 0.071 | 2.8986 |
| 57 | 3.008 | 0.3001 | 0.505 | 0.0000 | 0.069 | 0.0000 |
| 62 | 3.017 | 0.7009 | 0.513 | 1.5842 | 0.075 | 10.2941 |
| 67 | 3.029 | 1.0340 | 0.494 | −2.5841 | 0.078 | 13.0435 |
| 72 | 2.998 | −0.0867 | 0.504 | −0.5917 | 0.069 | 0.0000 |
| 53 | 3.071 | 0.4580 | 1.033 | 0.1940 | 0.248 | 0.0000 |
| 58 | 2.998 | 0.4692 | 1.025 | 1.0848 | 0.238 | 0.4219 |
| 68 | 3.064 | 3.3738 | 1.053 | 4.0514 | 0.260 | 3.5857 |
| 73 | 2.991 | 0.1004 | 1.012 | 0.0000 | 0.244 | 0.0000 |
| 54 | 3.053 | 0.3616 | 1.009 | 0.3980 | 0.285 | 2.8881 |
| 59 | 3.036 | 0.0989 | 1.012 | 0.5964 | 0.285 | 2.5180 |
| 64 | 3.068 | 0.2942 | 1.012 | −0.2956 | 0.282 | 2.5455 |
| 69 | 3.020 | 1.1725 | 1.079 | 0.6530 | 0.284 | 3.6496 |
| 74 | 2.959 | −0.1687 | 1.015 | −0.0984 | 0.278 | 0.0000 |
| 55 | 2.970 | 0.3378 | 1.012 | 0.5964 | 0.247 | 2.0661 |
| 80 | 2.989 | 0.3020 | 1.019 | −0.0980 | 0.246 | 2.5000 |
| 85 | 2.992 | 0.5039 | 1.024 | 0.7874 | 0.259 | 5.2846 |
| 70 | 2.956 | 0.0000 | 1.029 | 1.4793 | 0.264 | 9.0909 |
| 75 | 2.937 | 0.0341 | 1.014 | −0.2950 | 0.247 | 0.0000 |

| Test item | Test Solution | Material RUBBERS | Visual Observations |
|---|---|---|---|
| 51 | (A) 500 ppm POAA/Buffered | Silicone | A dull, med. - dark orange material similar to control |
| 56 | (B) 5000 ppm POAA/Buffered | Silicone | A dull, med. - dark orange material similar to control |
| 61 | (C) 500 ppm POAA only | Silicone | A dull, med. - dark orange material similar to control |
| 66 | (D) 5000 ppm POAA only | Silicone | A dull, med. - dark orange material similar to control |
| 71 | CONTROL | Silicone | A dull, med. - dark orange material |
| 52 | (A) 500 ppm POAA/Buffered | Butyl | A dull black material with slt. tacky, slt. rough surface that stuck to drying surface resulting in loss of material |
| 57 | (B) 5000 ppm POAA/Buffered | Butyl | A dull black material with very slt. tacky, smooth surface |
| 62 | (C) 500 ppm POAA only | Butyl | A black material with tacky, dull, rough surface that stuck to drying surface resulting in loss of material |

-continued

PART IV: CORROSION - RUBBERS
Analytical - Observations
KX-6091 CORROSION STUDY
14 day Compatibility Test of 15 different materials tested against four different Test
Solutions at 50° C. with the test solutions are changed daily.

| 67 | (D) 5000 ppm POAA only | Butyl | A dull black material with very tacky, very rough, surface that stuck to drying surface resulting in loss of material |
| 53 | (A) 500 ppm POAA/Buffered | Vison | A dull, charcoal black material with smooth surface |
| 58 | (B) 5000 ppm POAA/Buffered | Vison | A dull, charcoal black material with smooth surface |
| 63 | (C) 500 ppm POAA only | Vison | A dull, charcoal black material with slt. rough surface |
| 68 | (D) 5000 ppm POAA only | Vison | A dull, charcoal black material with slt. rough surface |
| 73 | CONTROL | Vison | A dull, charcoal black material with smooth surface |
| 54 | (A) 500 ppm POAA/Buffered | EPDM | A dull, black material with slt. rough surface |
| 59 | (B) 5000 ppm POAA/Buffered | EPDM | A dull, black material with slt. blistered surface |
| 64 | (C) 500 ppm POAA only | EPDM | A dull, black material with slt. rough surface |
| 69 | (D) 5000 ppm POAA only | EPDM | A dull black material with slt. rough surface containing a large blister |
| 74 | CONTROL | EPDM | A dull, black material with smooth surface |
| 55 | (A) 500 ppm POAA/Buffered | BUNA N | A dull, (darker than control) black material with slt. rough surface |
| 60 | (B) 5000 ppm POAA/Buffered | BUNA N | A dark black material with very slt. shiny, fairly smooth surface |
| 65 | (C) 500 ppm POAA only | BUNA N | A dark black material with very slt. shiny, slt. blistered surface |
| 70 | (D) 5000 ppm POAA only | BUNA N | A dark black material with very slt. shiny, blistered surface |
| 75 | CONTROL | BUNA N | A dull, grayish black material with smooth surface |

I. Tuberculocidal Efficacy US Method

The peracetic acid product was tested against *Mycobacterium bovis* (BCG) using the AOAC Confirmatory Test with product concentrations as listed below. The product was diluted in buffer to achieve the pH 6 prior to test. The diluent tested was either tap or distilled water. Test exposure time was 10 minutes. A result of ten no growth tubes per ten tubes tested is required for a passing result. Conclusion: successful tuberculocidal results were achieved a product concentrations as low as 1000 ppm POAA.

| Product Concentration[a] | Number of no growth tubes/ number of tubes tested[b] |
|---|---|
| 1000 ppm POAA | 10/10 - pass |
| 2000 ppm POAA | 10/10 - pass |
| 3000 ppm POAA | 10/10 - pass |
| 4000 ppm POAA | 10/10 - pass |
| 5000 ppm POAA | 10/10 - pass |

[a]Diluent was tap or distilled water with pH adjusted to 6.

-continued

| Product Concentration[a] | Number of no growth tubes/ number of tubes tested[b] |
|---|---|

[b]Test results reflect data achieved in three test media, Proskauer-Beck, Kirshners and Middlebrook.

II. Suspension Test—Olympus Method

We have completed the suspension test as requested with the Olympus procedure versus *Bacillus subtilis*. The product was diluted in buffer to achieve the pH 6 prior to test. The diluent tested was tap water. Test exposure times are listed below. The data are represented as log reduction of bacterial numbers. Note: the spores were counted after the heat shock treatment, although the test was conducted on a non-heat treated bacterial suspension. Conclusion significant log reductions in microbial numbers were achieved within 10 minutes using 500 ppm POAA. Additional product concentration or exposure time did not increase the efficacy of the product.

| | *Bacillus subtilis* Log Reduction at 20° C. (ppm POAA) | | | | |
|---|---|---|---|---|---|
| Exposure time (minutes) | 250 ppm | 500 ppm | 1000 ppm | 1500 ppm (Henkel-Ecolab test only) | 2000 ppm (Ecolab test only) |
| 5 minutes | 4.55 | 6.13 | 9.48 | 7.70 | 9.78 |
| 10 minutes | 7.98 | 9.78 | 9.78 | 7.68 | 9.78 |
| 20 minutes | 9.48 | 9.78 | 9.78 | 7.71 | 9.78 |
| 60 minutes | 9.48 | 9.78 | 9.78 | 7.74 | 9.78 |

-continued

| Exposure time (minutes) | Bacillus subtilis Log Reduction at 20° C. (ppm POAA) | | | | |
|---|---|---|---|---|---|
| | 250 ppm | 500 ppm | 1000 ppm | 1500 ppm (Henkel-Ecolab test only) | 2000 ppm (Ecolab test only) |
| Neutralization control | | | | | 0.10[A] |
| Total inoculum | | | | $3.4 \times 10^8$ cfu/ml | $6.0 \times 10^9$ cfu/ml |
| Spore inoculum | | | | $9.0 \times 10^6$ cfu/ml | $3.3 \times 10^5$ cfu/ml |

[A]Neutralizer is 1 % sodium thiosulfate and is effective in this test procedure for chemical neutralization of the test substance.

III. Carrier Test—Olympus Method

We have completed the carrier test as requested using the Olympus procedure versus *Bacillus subtilis* and *Mycobacterium terrae*. The product was diluted in buffer to achieve the pH 6 prior to test The diluent tested was tap water. Test exposure times are listed below. Note: the spores were counted after the heat shock treatment although the test was conducted on a non-heat treated bacterial suspensions. Conclusion: successful results achieved using 250 ppm POAA within five minutes exposure against both subtilis and *Mycobacterium terrae*. Additional product concentration or exposure time did not increase the efficacy of the product.

| Product Concentration[a] | Exposure Time | Number of no growth tubes/ number of tubes tested[b] | |
|---|---|---|---|
| | | Primary Subculture | Secondary Subculture |
| 4000 ppm POAA | 3 hours | 20/20 | 0/20 |
| | 4 hours | 20/20 | 1/20 |
| | 6 hours | 19/20 | 20/20 |
| 5000 ppm POAA | 3 hours | 19/20 | 6/20 |

| Exposure time (minutes) | 250 ppm | | | 1000 ppm | | | 2500 ppm | | | 5000 ppm | | |
|---|---|---|---|---|---|---|---|---|---|---|---|---|
| | CARRIER RESULTS[A] | A[B] | B[C] | CARRIER RESULTS | A | B | CARRIER RESULTS | A | B | CARRIER RESULTS | A | B |
| *Bacillus subtilis* at 20° C. (ppm POAA) | | | | | | | | | | | | |
| 0 minutes | | | | | | | | | | 0/2 | $2.3 \times 10^4$ | $1.9 \times 10^3$ |
| 5 minutes | 2/2 | <1 | <1 | 2/2 | <1 | <1 | 2/2 | <1 | <1 | 2/2 | <1 | <1 |
| 10 minutes | 2/2 | <1 | <1 | 2/2 | <1 | <1 | 2/2 | <1 | <1 | 2/2 | <1 | <1 |
| 20 minutes | 2/2 | <1 | <1 | 2/2 | <1 | <1 | 2/2 | <1 | <1 | 2/2 | <1 | <1 |
| 60 minutes | 2/2 | <1 | <1 | 2/2 | <1 | <1 | 2/2 | <1 | <1 | 2/2 | <1 | <1 |
| *Mycobacterium terrae* at 20° C. (ppm POAA) | | | | | | | | | | | | |
| 0 minutes | | | | | | | | | | 0/2 | $3.2 \times 10^3$ | $2.1 \times 10^4$ |
| 5 minutes | 2/2 | <1 | <1 | 2/2 | <1 | <1 | 2/2 | <1 | <1 | 2/2 | <1 | <1 |
| 10 minutes | 2/2 | <1 | <1 | 2/2 | <1 | <1 | 2/2 | <1 | <1 | 2/2 | <1 | <1 |
| 20 minutes | 2/2 | <1 | <1 | 2/2 | <1 | <1 | 2/2 | <1 | <1 | 2/2 | <1 | <1 |
| 60 minutes | 2/2 | <1 | <1 | 2/2 | <1 | <1 | 2/2 | <1 | <1 | 2/2 | <1 | <1 |

[A]Number of negative carriers per number of carriers tested.
[B]Plate A is the average cfu/ml of product plus neutralizer mixture.
[C]Plate B is the average cfu/ml of stripper.
[D]Neutralizer is 1% sodium thiosulfate and is effective in this test procedure for chemical neutralization of the test substance.

IV. Sporicidal Efficacy—US Method

The peracetic acid product was tested against *Clostridium sporogenes* using the AOAC Sporicdal Activity of Disinfectants Test with product concentrations as listed below. The product was diluted in buffer to achieve the pH 6 prior to test The diluent tested was tap water. Test exposure time was 3, 4 or 6 hours. A result of twenty no growth tubes per twenty tubes tested is required for a passing result. Conclusion: successful results were achieved at 5000 ppm POM with an exposure time of 6 hours.

-continued

| Product Concentration[a] | Exposure Time | Number of no growth tubes/ number of tubes tested[b] | |
|---|---|---|---|
| | | Primary Subculture | Secondary Subculture |
| | 4 hours | 20/20 | 17/20 |
| | 6 hours | 20/20 | 20/20 |

-continued

| Product Concentration[a] | Exposure Time | Number of no growth tubes/number of tubes tested[b] | |
|---|---|---|---|
| | | Primary Subculture | Secondary Subculture |
| 7000 ppm POAA | 3 hours | 20/20 | 10/20 |
| | 4 hours | 20/20 | 11/20 |
| | 6 hours | 20/20 | 20/20 |

[a]Diluent was tap or distilled water with pH adjusted to 6.
[b]Test results reflect data achieved in three test media, Proskauer-Beck, Kirshners and Middlebrook after heat-shock treatment and reincubation for 72 hours.

OBJECTIVE:

The objective of this analysis was to evaluate the effect of hydrogen peroxide and acetic acid concentration on the sporicidal efficacy of 150 ppm peracetic acid at 40° C.

TEST METHOD:

Ecolab Microbiological Services SOP CB021-04; Rate of Kill Antimicrobial Efficacy. Following exposure to the formula and subsequent neutralization, spores were heat shocked for 13 minutes at 80° C. before plating.

METHOD PARAMETERS:

Test Substances: Each formula was prepared using a "stock" POAA material (34.1% POAA, 7.13% $H_2O_2$ and 36.1% acetic acid—Aldrich Chemical) to achieve 150 ppm POAA. $H_2O_2$ or acetic acid was then added as needed. Please refer to the data sheet attached to this report for preparation information. Since chemical analyses of solutions prepared exactly like those prepared for this study were done previously, and concentrations were found to be accurate, additional chemical analysis for this study was not performed (see MSR #960351, J. Hilgren).

| Chemical Properties of Each Test Formula | | | | |
|---|---|---|---|---|
| Formula | Theoretical ppm POAA | Theoretical ppm $H_2O_2$ | Theoretical ppm Acetic Acid | pH |
| A | 150 | 31 | 159 | 3.75 |
| B | 150 | 31 | 309 | 3.67 |
| C | 150 | 275 | 159 | 3.75 |
| D | 150 | 275 | 309 | 3.68 |
| E | 150 | 529 | 159 | 3.77 |
| F | 150 | 329 | 309 | 3.68 |

Test System: *Bacillus cereus* spore crop N1009
Test Temperature: 40° C.
Exposure Times: 0.5, 1.0, 1.5, 2.0, 2.5, 3.0 and 3.5 hours
Neutralizer: Fluid Thioglycollate Medium
Plating Media: Dextrose Tryptone Agar
Incubation: 32° C. for 48 hours

RESULTS:

| | Inoculum Numbers | | | |
|---|---|---|---|---|
| | Inoculum Test Replicate (CFU/mL) | | | Average |
| Organism | 1 | 2 | 3 | (CFU/mL) |
| *B. cereus* Spores | $30 \times 10^6$ | $26 \times 10^6$ | $26 \times 10^6$ | $2.7 \times 10^7$ |

Reduction of *B. cereus* Spores at 40° C.

| Formula | Exposure Time (hours) | Survivors (CFU/mL) | Log Reduction |
|---|---|---|---|
| A | 0.5 | $<1.0 \times 10^1$ | >6.43 |
| Low Acetic, | 1.0 | $<1.0 \times 10^1$ | >6.43 |
| Low $H_2O_2$ | 1.5 | $<1.0 \times 10^1$ | >6.43 |
| | 2.0 | $<1.0 \times 10^1$ | >6.43 |
| | 2.5 | $<1.0 \times 10^1$ | >6.43 |
| | 3.0 | $<1.0 \times 10^1$ | >6.43 |
| | 3.5 | $<1.0 \times 10^1$ | >6.43 |
| B | 0.5 | $<1.0 \times 10^1$ | >6.43 |
| High Acetic, | 1.0 | $<1.0 \times 10^1$ | >6.43 |
| Low $H_2O_2$ | 1.5 | $<1.0 \times 10^1$ | >6.43 |
| | 2.0 | $<1.0 \times 10^1$ | >6.43 |
| | 2.5 | $<1.0 \times 10^1$ | >6.43 |
| | 3.0 | $<1.0 \times 10^1$ | >6.43 |
| | 3.5 | $<1.0 \times 10^1$ | >6.43 |
| C | 0.5 | $1.7 \times 10^7$ | 0.20 |
| Low Acetic, | 1.0 | $6.0 \times 10^6$ | 0.65 |
| Medium $H_2O_2$ | 1.5 | $2.5 \times 10^6$ | 1.03 |
| | 2.0 | $9.0 \times 10^5$ | 1.48 |
| | 2.5 | $2.1 \times 10^5$ | 2.11 |
| | 3.0 | $6.0 \times 10^4$ | 2.65 |
| | 3.5 | $1.5 \times 10^4$ | 3.26 |
| D | 0.5 | $1.5 \times 10^7$ | 0.26 |
| High Acetic, | 1.0 | $4.9 \times 10^6$ | 0.74 |
| Medium $H_2O_2$ | 1.5 | $2.2 \times 10^6$ | 1.09 |
| | 2.0 | $4.6 \times 10^5$ | 1.77 |
| | 2.5 | $1.2 \times 10^5$ | 2.35 |
| | 3.0 | $3.1 \times 10^4$ | 2.94 |
| | 3.5 | $1.1 \times 10^4$ | 3.39 |
| E | 0.5 | $1.5 \times 10^7$ | 0.26 |
| Low Acetic, | 1.0 | $5.1 \times 10^6$ | 0.72 |
| High $H_2O_2$ | 1.5 | $1.4 \times 10^6$ | 1.29 |
| | 2.0 | $3.1 \times 10^5$ | 1.94 |
| | 2.5 | $3.4 \times 10^4$ | 2.90 |
| | 3.0 | $4.0 \times 10^3$ | 3.83 |
| | 3.5 | $5.6 \times 10^2$ | 4.68 |
| F | 0.5 | $1.4 \times 10^7$ | 0.29 |
| High Acetic, | 1.0 | $4.7 \times 10^6$ | 0.76 |
| High $H_2O_2$ | 1.5 | $1.7 \times 10^6$ | 1.20 |
| | 2.0 | $4.3 \times 10^5$ | 1.80 |
| | 2.5 | $3.3 \times 10^4$ | 2.91 |
| | 3.0 | $5.0 \times 10^3$ | 3.73 |
| | 3.5 | $8.1 \times 10^2$ | 4.52 |

Figure 3:
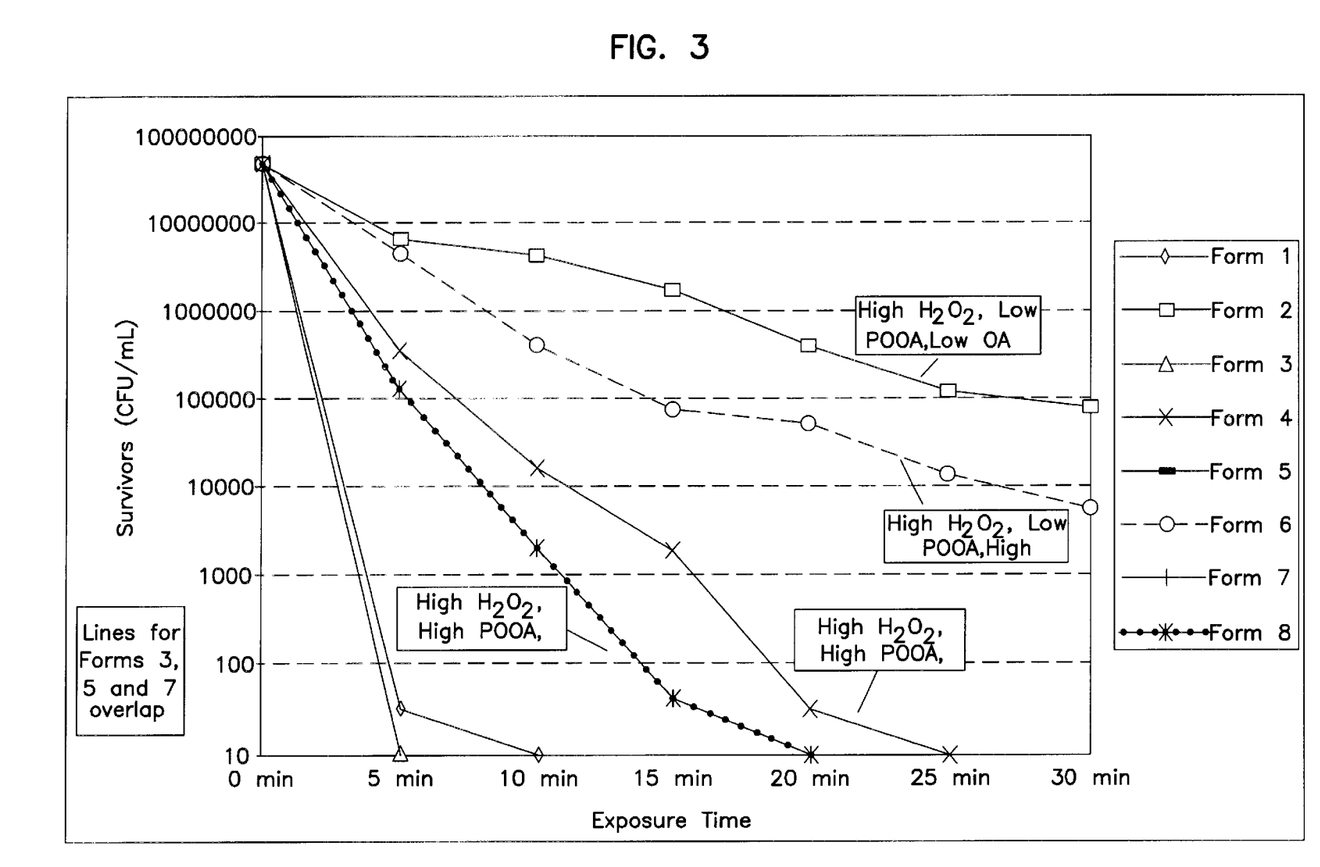
FIG. 3 is a graph showing the reduction of B. cereus spores at 40° C.

A graphical representation of the reduction of *B. cereus* spores at 40° C. is presented in FIG. 3. The lower limit of detection for the test procedure was 10 C.F.U./mL.

CONCLUSIONS:

The sporicidal activity of 150 ppm POAA at 40° C. against *Bacillus cereus* spores was most effective when in the presence of relatively low concentrations of $H_2O_2$ (≈330 ppm as in Formulas A and B). Reduced *B. cereus* sporicidal efficacy was observed using POAA with the medium and high concentrations of $H_2O_2$ (≈160 and 300 ppm as in Formulas C through F).

OBJECTIVE:

The objective of this analysis was to evaluate the effect of hydrogen peroxide and acetic acid concentration on the sporicidal efficacy of 150 ppm peracetic acid at 60° C.

TEST METHOD:

Ecolab Microbiological Services SOP CB021-04; Rate of Kill Antimicrobial Efficacy. Following exposure to the formula and subsequent neutralization, spores were heat shocked for 13 minutes at 80° C. before plating.

METHOD PARAMETERS:

Test Substances: Each formula was prepared using a "stock" POAA material (34.1% POAA, 7.13% $H_2O_2$ and 36.1% acetic acid—Aldrich Chemical) to achieve 150 ppm POAA. $H_2O_2$ or acetic acid was then added as needed. Please refer to the data sheet attached to this report for theoretical concentrations and preparation information.

| | Formula Properties (≈ 2 Hours Post Preparation/ After 40 min. at 60° C.) | | | |
|---|---|---|---|---|
| Formula | ppm POAA | ppm $H_2O_2$ | ppm Acetic Acid | pH |
| A | 147/144 | 31/33 | 174/166 | 3.76/3.67 |
| B | 145/144 | 33/37 | 346/346 | 3.71/3.55 |
| C | 151/148 | 277/281 | 141/143 | 3.79/3.69 |
| D | 151/151 | 283/280 | 301/291 | 3.70/3.60 |
| E | 157/154 | 526/514 | 136/148 | 3.81/3.71 |
| F | 160/159 | 533/240* | 293/324 | 3.71/3.62 |

*No obvious error in analysis was detected, but the result remains in question.

Test System: *Bacillus cereus* spore crop N1009
Test Temperature: 60° C.
Exposure Times: 10, 15, 20, 25, 30 and 40 minutes
Neutralizer: Fluid Thioglycollate Medium
Plating Media: Dextrose Tryptone agar
Incubation: 32° C. for 48 hours

| | Inoculum Numbers | | | |
|---|---|---|---|---|
| | Inoculum Test Replicate (CFU/mL) | | | Average |
| Organism | 1 | 2 | 3 | (CFU/mL) |
| *B. cereus* Spores | $28 \times 10^6$ | $22 \times 10^6$ | $29 \times 10^6$ | $2.6 \times 10^7$ |

| Reduction of *B. cereus* Spores at 60° C. | | | |
|---|---|---|---|
| Formula | Exposure Time (hours) | Survivors (CFU/mL) | Log Reduction |
| A | 10 | $<1.0 \times 10^1$ | >6.41 |
| Low Acetic, | 15 | $<1.0 \times 10^1$ | >6.41 |
| Low $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| B | 10 | $<1.0 \times 10^1$ | >6.41 |
| High Acetic, | 15 | $<1.0 \times 10^1$ | >6.41 |
| Low $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| C | 10 | $4.1 \times 10^4$ | 2.80 |
| Low Acetic, | 15 | $2.0 \times 10^2$ | 5.11 |
| Medium $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| D | 10 | $2.6 \times 10^4$ | 3.00 |
| High Acetic, | 15 | $7.0 \times 10^1$ | 5.57 |
| Medium $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| E | 10 | $2.4 \times 10^4$ | 3.03 |
| Low Acetic, | 15 | $2.4 \times 10^2$ | 5.03 |
| High $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| F | 10 | $1.1 \times 10^4$ | 3.37 |
| High Acetic, | 15 | $7.0 \times 10^1$ | 5.57 |
| High $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |

Figure 1:
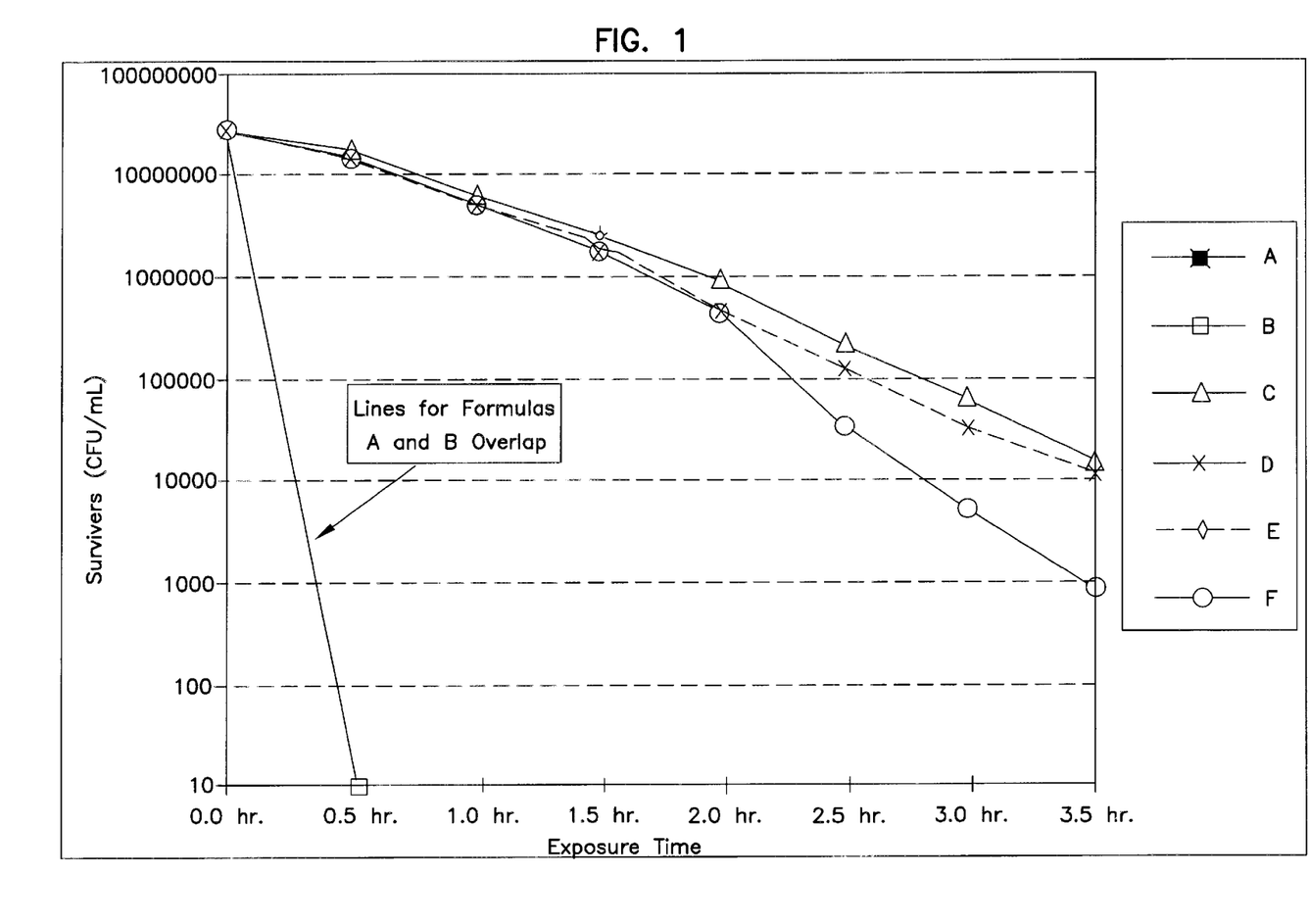
FIG. 1 is a graph showing the reduction of B. cereus spores at 40° C.
Figure 2:
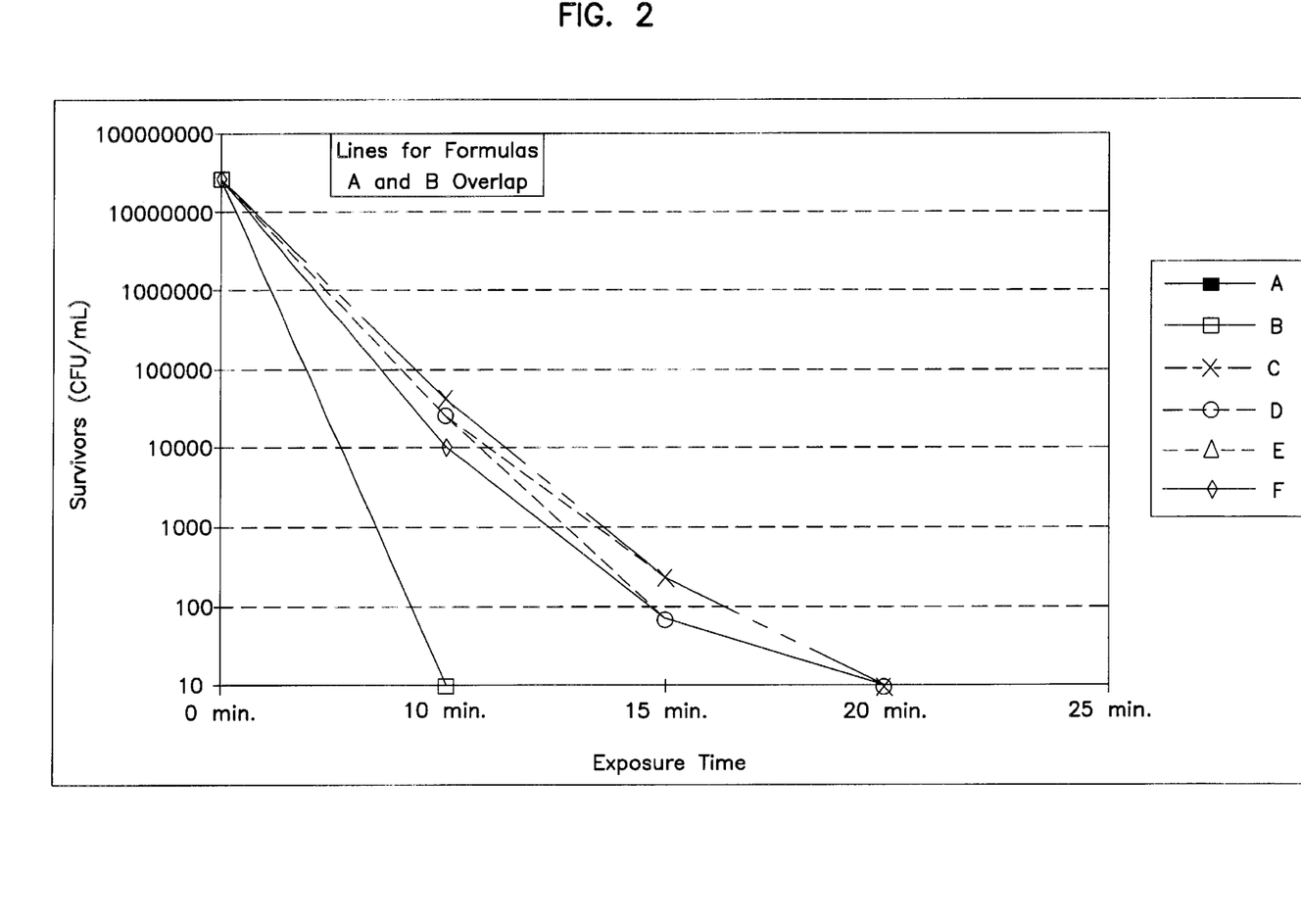
FIG. 2 is a graph showing the reduction of B. cereus spores at 60° C.

A graphical representation of the reduction of *B. cereus* spores at 60° C. It is shown in FIG. 2. The lower limit of detection for the test procedure was 10 C.F.U./mL.

CONCLUSIONS

The sporicidal activity of 150 ppm POAA at 60° C. against *Bacillus cereus* spores was most effective when in the presence of relatively low concentrations of $H_2O_2$ (≈160 and 300 ppm as in Formulas C through F).

Further testing using Formulas A–F will be conducted at 20° C. to determine the effect of $H_2O_2$ and acetic acid concentration on sporicidal efficacy of POAA at low temperature.

OBJECTIVE:

The objective of this analysis was to evaluate the effect of hydrogen peroxide, octanoic acid and peroctanoic acid concentration on the sporicidal efficacy of 150 ppm peracetic acid at 40° C.

TEST METHOD:

Ecolab Microbiological Services SOP CB021-04; Rate of Kill Antimicrobial Efficacy. Following exposure to the formula and subsequent neutralization, spores were heat shocked for 13 minutes at 80° C. before plating.

METHOD PARAMETERS:

Test Substances: Each formula was prepared using a "stock" POAA material (33.5% POAA, 7.03% $H_2O_2$ and 37.2% acetic acid—Aldrich Chemical) and a "stock" octanoic/peroctanoic material (11.4% octanoic, 3.4% POOA 10.29% POAA, 3.70% $H_2O_2$—Falcon 15). Hydrogen peroxide, octanoic acid or peroctanoic acid were then added as needed. Please refer to the data sheet attached to this report for preparation information. Prior to this study, chemical analyses of formulas exactly like those used for this study were conducted to determine if ingredient concentrations were close to theoretical and if they were stable over the duration of the efficacy test. Results showed ingredient concentrations to correlate with theoretical and to be stable.

Chemical Properties of Each Test Formula

| Formula | Theoretical ppm POAA | Theoretical ppm $H_2O_2$ | Theoretical ppm AA | Theoretical ppm POOA | Theoretical ppm OA | pH |
|---|---|---|---|---|---|---|
| 1 | 149 | 36  | 282 | 12 | 39  | 3.65 |
| 2 | 149 | 529 | 282 | 12 | 39  | 3.62 |
| 3 | 149 | 36  | 282 | 50 | 39  | 3.64 |
| 4 | 149 | 529 | 282 | 50 | 39  | 3.63 |
| 5 | 149 | 36  | 282 | 12 | 138 | 3.64 |
| 6 | 149 | 529 | 282 | 12 | 138 | 3.63 |
| 7 | 149 | 36  | 282 | 50 | 138 | 3.64 |
| 8 | 149 | 529 | 282 | 50 | 138 | 3.65 |

Test System: *Bacillus cereus* spore crop N1009

Test Temperature: 40° C.

Exposure Times: 5, 10, 15, 20, 25 and 30 minutes

Neutralizer: Fluid Thioglycollate Medium

Plating Medium: Dextrose Tryptone Agar

Incubation; 32° C. for 48 hours

RESULTS

Inoculum Numbers

| Organism | Inoculum Test Replicate (CFU/mL) 1 | 2 | 3 | Average (CFU/mL) |
|---|---|---|---|---|
| *B. cereus* Spores | $56 \times 10^6$ | $42 \times 10^6$ | $35 \times 10^6$ | $4.4 \times 10^7$ |

Reduction of *B. cereus* Spores at 40° C.

| Formula | Exposure Time (hours) | Survivors (CFU/mL) | Log Reduction |
|---|---|---|---|
| 1 | 5 | $3.0\times10^1$ | 6.17 |
| Low $H_2O_2$, | 10 | $<1.0\times10^1$ | >6.64 |
| Low POOA, | 15 | $<1.0\times10^1$ | >6.64 |
| Low OA | 20 | $<1.0\times10^1$ | >6.64 |
| | 25 | $<1.0\times10^1$ | >6.64 |
| | 30 | $<1.0\times10^1$ | >6.64 |
| 2 | 5 | $6.4\times10^6$ | 0.84 |
| High $H_2O_2$, | 10 | $4.3\times10^6$ | 1.01 |
| Low POOA, | 15 | $1.8\times10^6$ | 1.39 |
| Low OA | 20 | $4.0\times10^5$ | 2.04 |
| | 25 | $1.2\times10^5$ | 2.56 |
| | 30 | $8.1\times10^4$ | 2.73 |
| 3 | 5 | $<1.0\times10^1$ | >6.64 |
| Low $H_2O_2$, | 10 | $<1.0\times10^1$ | >6.64 |
| High POOA, | 15 | $<1.0\times10^1$ | >6.64 |
| Low OA | 20 | $<1.0\times10^1$ | >6.64 |
| | 25 | $<1.0\times10^1$ | >6.64 |
| | 30 | $<1.0\times10^1$ | >6.64 |
| 4 | 5 | $3.4\times10^5$ | 2.11 |
| High $H_2O_2$, | 10 | $1.6\times10^4$ | 3.44 |
| High POOA, | 15 | $1.9\times10^3$ | 4.36 |
| Low OA | 20 | $3.0\times10^1$ | 6.17 |
| | 25 | $<1.0\times10^1$ | >6.64 |
| | 30 | $<1.0\times10^1$ | >6.64 |
| 5 | 5 | $<1.0\times10^1$ | >6.64 |
| Low $H_2O_2$, | 10 | $<1.0\times10^1$ | >6.64 |
| Low POOA, | 15 | $<1.0\times10^1$ | >6.64 |
| High OA | 20 | $<1.0\times10^1$ | >6.64 |
| | 25 | $<1.0\times10^1$ | >6.64 |
| | 30 | $<1.0\times10^1$ | >6.64 |
| 6 | 5 | $4.4\times10^6$ | 1.00 |
| High $H_2O_2$, | 10 | $4.1\times10^5$ | 2.03 |
| Low POOA, | 15 | $7.7\times10^4$ | 2.76 |
| High OA | 20 | $5.3\times10^4$ | 2.92 |
| | 25 | $1.4\times10^4$ | 3.50 |
| | 30 | $5.8\times10^3$ | 3.88 |

-continued

| | | | |
|---|---|---|---|
| 7 | 5 | $<1.0\times10^1$ | >6.64 |
| Low $H_2O_2$, | 10 | $<1.0\times10^1$ | >6.64 |
| High POOA, | 15 | $<1.0\times10^1$ | >6.64 |
| High OA | 20 | $<1.0\times10^1$ | >6.64 |
| | 25 | $<1.0\times10^1$ | >6.64 |
| | 30 | $<1.0\times10^1$ | >6.64 |
| 8 | 5 | $1.2\times10^5$ | 2.56 |
| High $H_2O_2$, | 10 | $2.0\times10^3$ | 4.34 |
| High POOA, | 15 | $4.0\times10^1$ | 6.04 |
| High OA | 20 | $<1.0\times10^1$ | >6.64 |
| | 25 | $<1.0\times10^1$ | >6.64 |
| | 30 | $<1.0\times10^1$ | >6.64 |

A graphical representation of the reduction of *B. cereus* spores at 40° C. is presented in FIG. 1. The lower limit of detection for the test procedure was 10 C.F.U./mL.

CONCLUSIONS:

Effect of $H_2O_2$:

The sporicidal activity of 150 ppm POAA at 40° C. against *Bacillus cereus* spores was most effective when in the presence of relatively low concentrations of $H_2O_2$ (≈36 ppm as in Formulas 1, 3, 5 and 7). Reduced *B. cereus* sporicidal efficacy was observed using POAA with the higher concentrations of $H_2O_2$ (≈529 ppm as in Formulas 2, 4, 6 and 8).

Effects of Octanoic and Peroctanoic Acid:

The sporicidal activity of 150 ppm POAA at 40° C. against *Bacillus cereus* spores increased when the concentrations of octanoic or peroctanoic acid increased. This phenomenon was clearly evident in formulas containing the high concentrations of $H_2O_2$ (formulas 2, 4, 6 and 8).

On a weight basis, peroctanoic acid had a greater effect on the sporicidal efficacy of 150 ppm POAA against *B. cereus* than octanoic acid. An increase of 38 ppm POOA resulted in a greater log reduction of *B. cereus* spores than an increase of 99 ppm octanoic acid. An additive effect was observed when POOA and octanoic acid were combined.

What is claimed:

1. A method of sterilizing an article comprising:

(a) mixing a first aqueous solution and a second aqueous solution to form a sterilizing solution comprising at least 100 ppm peroxy acid and a sufficient amount of phosphate buffering agent to provide the sterilizing solution with a pH of about 5 to about 7, wherein:

(i) the first aqueous solution comprises a mixture of carboxylic acid, hydrogen peroxide, and water, and (ii) the second aqueous solution comprises phosphate buffering agent and water; and (b) immersing the article in the sterilizing solution for at least 5 minutes to sterilize the article;

wherein the sterilizing solution contains no effective amount of organic corrosion inhibitor and has a weight ratio of peroxy acid to hydrogen peroxide of at least 2:1.

2. A method according to claim 1, wherein the phosphate buffering agent comprises trisodium phosphate.

3. A method according to claim 1, wherein the sterilizing solution comprises a catalytic amount of a catalyst for peroxidation of the carboxylic acid by the hydrogen peroxide.

4. A method according to claim 1, wherein the peroxy acid comprises a peroxy acid of at least one C1 to C12 carboxylic acid.

5. A method according to claim 1, wherein the peroxy acid comprises a peroxy acid of at least one C1 to C8 carboxylic acid.

6. A method according to claim 1, wherein the sterilizing solution comprises 1000 to 5000 ppm peroxy acid.

7. A method according to claim 1, wherein the peroxy acid comprises at least one of performic acid, peracetic acid, perpropionic acid, perbutanoic acid, perpentanoic acid, perhexanoic acid, perheptanoic acid, peroctanoic acid, pernonanoic acid, perundecanoic acid, and perdecanoic acid.

8. A method according to claim 1, wherein the first aqueous solution further comprises peroxycarboxylic acid.

9. A method according to claim 1, wherein the article comprises a polymeric material.

10. A method according to claim 9, wherein the polymeric material comprises at least one of polypropylene, polytetrafluoroethylene, acrylonitrile/styrene/butadiene, polyolefin, polyvinyl chloride, polyvinyl butyrel, silicone resins, rubber, and polyurethane.

11. A method for sterilizing according to claim 1, wherein the article comprises at least one of stainless steel, aluminum, brass, and copper.

* * * * *